United States Patent
Heid

(10) Patent No.: US 7,861,632 B2
(45) Date of Patent: Jan. 4, 2011

(54) KNIFE HOLDER FOR A MICROTOME

(75) Inventor: Hans Heid, Bammental (DE)

(73) Assignee: MICROM International GmbH, Walldorf (DE)

( * ) Notice: Subject to any disclaimer, the term of this patent is extended or adjusted under 35 U.S.C. 154(b) by 244 days.

(21) Appl. No.: 11/446,237

(22) Filed: Jun. 5, 2006

(65) Prior Publication Data

US 2006/0219080 A1 Oct. 5, 2006

Related U.S. Application Data

(63) Continuation of application No. 09/770,958, filed on Jan. 25, 2001, now abandoned, which is a continuation of application No. PCT/EP99/03175, filed on May 10, 1999.

(30) Foreign Application Priority Data

May 29, 1998 (DE) ................. 198 24 024

(51) Int. Cl.
*G01N 1/06* (2006.01)
(52) U.S. Cl. .............. 83/397; 83/713; 83/546; 83/915.5
(58) Field of Classification Search ............ 83/397, 83/425, 435.11, 437.1, 440.2, 544, 545, 546, 83/703, 713, 733, 856, 915.5, DIG. 1; 30/286, 30/295
See application file for complete search history.

(56) References Cited

U.S. PATENT DOCUMENTS

| 52,948 | A | * | 3/1866 | Forsyth ............. 172/752 |
| 793,793 | A | * | 7/1905 | Kampfe .............. 30/27 |
| 1,925,181 | A | * | 9/1933 | Fassin ............... 83/433 |
| 2,647,439 | A | * | 8/1953 | Roofe et al. .......... 269/13 |
| 3,515,192 | A | * | 6/1970 | Ducourneau .......... 83/86 |
| 4,024,779 | A | * | 5/1977 | Taugner et al. ....... 83/165 |
| 4,502,358 | A | * | 3/1985 | Behme ............. 83/699.61 |
| 5,282,404 | A | * | 2/1994 | Leighton et al. ....... 83/13 |
| 5,477,760 | A | * | 12/1995 | Kuchler ............. 83/58 |
| 5,678,465 | A | * | 10/1997 | Krumdieck .......... 83/36 |
| 5,784,936 | A | * | 7/1998 | King ............... 83/145 |
| 5,851,213 | A | * | 12/1998 | Berleth et al. ........ 606/167 |

FOREIGN PATENT DOCUMENTS

JP 55-148902 4/1954

* cited by examiner

*Primary Examiner*—Kenneth E. Peterson
(74) *Attorney, Agent, or Firm*—Paul Vincent

(57) ABSTRACT

A knife holder for a microtome has a plate arranged pivotably on its base member, which, in its functional position, covers the cutting edge of the knife and is spaced apart from the cutting plane towards the side of the knife holder remote from the specimen. The plate is also spaced apart from the knife holder on the side of the cutting edge of the knife. The plate precludes gripping of the cutting edge of the knife and a pivoting mechanism for the plate is coupled to a switch. When the plate is pivoted out of the functional position, the motor drive of the cutting movement is locked, or a brake precludes any movement of the knife slide or specimen slide. The plate preferably consists of a transparent material to permit observation of section removal in the functional position.

4 Claims, 5 Drawing Sheets

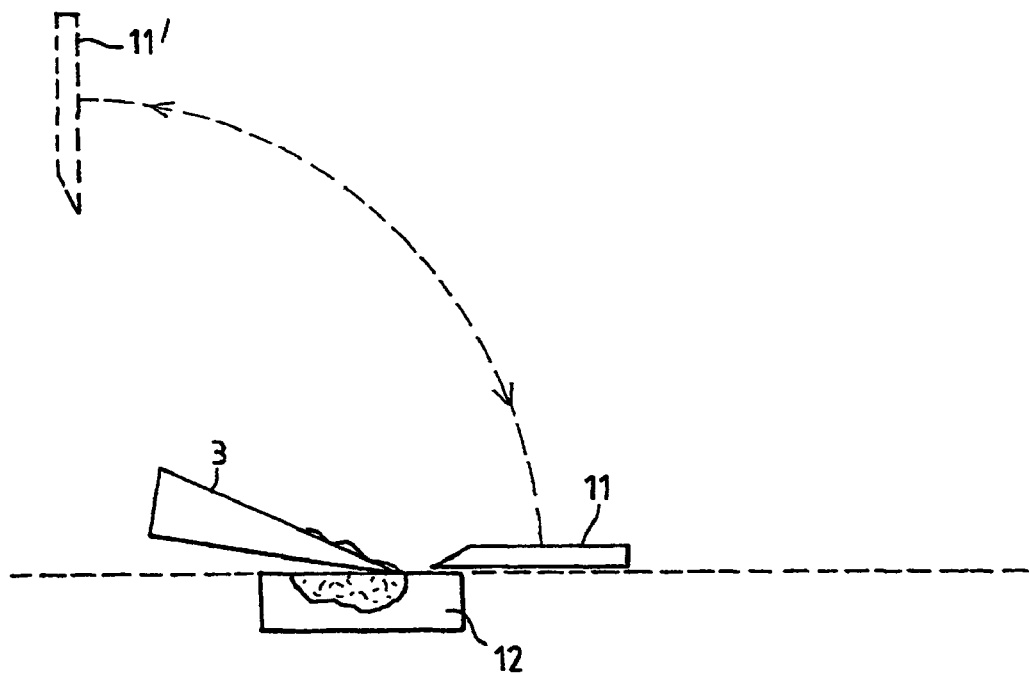
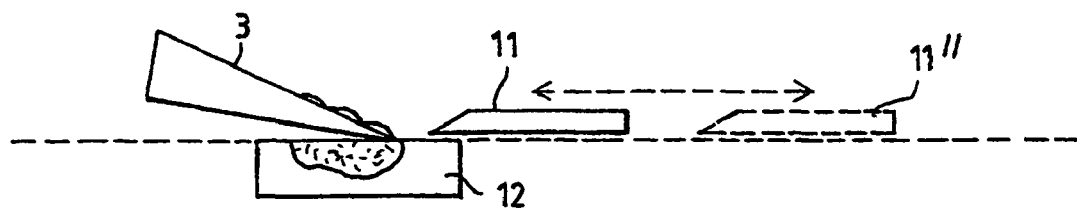

KNIFE HOLDER FOR A MICROTOME

This application is a continuation of Ser. No. 09/770,958 filed Jan. 25, 2001 as a continuation of International Application PCT/EP99/03175, with an international filing date of May 10, 1999, now abandoned, the entire disclosures of which are both hereby incorporated by reference.

BACKGROUND OF THE INVENTION

Microtomes are used for the production of thin sections of various specimens from medicine, biology, botany, and the materials research and quality control of technical materials, principally plastics. The production of these thin sections is effected using knives of various shapes and properties. Steel knives of selected tool steels are known, and are produced with various kinds of grinding. In addition to these regrindable knives, so-called disposable blades are widely used; for these, a distinction is principally made between so-called wide band blades and narrow band blades, which are replaced by new ones when their service life is exceeded. Furthermore, glass knives and diamond knives are used for special purposes.

Many knife carriers and holders for all kinds of knives are known in microtome technology; they additionally differ in their constitution according to the type of microtome they are provided for. These types are chiefly differentiated as rotary microtomes, in which the specimen is moved in the vertical direction towards a stationary knife, for section removal; slide microtomes, in which either the knife holder or the specimen holder is moved in a horizontal direction for section removal; and disk microtomes, in which the specimen is arranged on a disk which rotates relative to a stationary knife, for section removal. Microtomes which are used in microtome cryostats correspond to these types and differ solely by a rustproof embodiment.

The knife carriers and knife holders have the principal purpose of stably clamping the respective cutting tool, in order to attain the result of cutting in the form of a thin section of, for example, 3μ. In addition to a stable clamping, which prevents vibrations of the knife, most knife carriers and knife holders have devices for free angular adjustment between the knife edge and the specimen. Further features of typical knife carriers and knife holders are height adjustment devices for the knife to be clamped, clamp devices for fixing the knife carrier and knife holder on a microtome base plate or a microtome base frame, and also, in the case of knife carriers and knife holders for cryostatic microtomes, so-called section path devices. Knife carriers and knife holders are denoted hereinafter, for simplification, simply as knife holders.

When working with microtomes there always exists a danger of cuts to the hand from the microtome knife. Finger guards are therefore frequently provided, and have to be brought into their functional position, in which they cover the knife, in each working pause and in each preliminary operation of clamping the specimen in the specimen holder, or when adjusting the knife. In some known knife holders, the finger guard is arranged pivotably on the knife holder for this purpose. Other finger protection devices are not connected to the knife holder and can be set freely on the knife. In such cases they are frequently held in their position by means of weak magnets, or are positioned by pins. Furthermore, other finger protection devices consist of sideways displaceable rods or guard plates, which can be displaced so that they cover the middle cutting region of the knife edge during work pauses. These finger protection devices all have the disadvantage that they offer no protection during operation, that is, when a series of sections are cut on the microtome. Corresponding finger protection devices are described, for example, in U.S. Pat. No. 5,099,735 and GP patent 2,238,973.

A knife holder is described in U.S. Pat. No. 4,378,719 with covering elements for the cutting edge of the knife which are stationary relative to the knife. However, the covering elements only incompletely cover the blade. A knife holder with a section straightener, which likewise partially covers the blade, is described in U.S. Pat. No. 5,050,470.

Microtomes with knife holders are respectively described in U.S. Pat. No. 1,925,181 and U.S. Pat. No. 5,161,446, in which the above mentioned disadvantages are avoided. The finger protection devices described therein respectively have a cover plate for the knife edge, pivotably arranged on the base body of the knife holder, on the specimen side of the knife. When the specimen holder and the knife come close together, this cover plate is pivoted, by means of a driver cam, out of its functional position in which it covers the cutting edge of the knife, and thus first releases the cutting edge of the knife directly before the section removal. The cutting edge of the knife remains free, however, after a successful section removal, until the specimen holder has become separated again from the knife to such an extent that there is no longer any contact between the driver cam and the specimen holder. Therefore these protective devices cannot offer any effective protection from cutting injuries in this phase of the cutting process. Apart from this, the possibility also exists, when cutting specimens with relatively short dimensions in the direction of the cutting edge of the knife, of a finger inadvertently getting between the specimen and the knife blade when the cutting edge is already exposed, and thus suffering an injury.

It is therefore the object of the invention to provide a knife holder with a guard against cutting injuries which is also effective during the performance of cutting operations and section removal.

SUMMARY OF THE INVENTION

This object is achieved by a microtome knife holder having a cutting plane, comprising a knife having a cutting edge, and a blade guard comprising a plate, wherein the plate is arranged on a side of the knife remote from a specimen side and spaced apart from the cutting plane at the side of the cutting edge of the knife. Advantageous configurations of the invention will become apparent from the detailed description.

The knife holder according to the invention has a blade guard made from a plate. The plate is then arranged, on the side of the knife remote from the specimen side, spaced apart from the cutting plane of the knife to be received in the knife holder or of the blade to be received in the knife holder, and to the side of the cutting edge.

Such a structure of the blade guard does not need to be removed for the removal of sections. It is thus fully effective during the removal of sections, and can extend over the whole length of the knife or over the whole length of the knife or blade usually exposed for section removal.

The plate is preferably arranged parallel to the knife surface, spaced from the cutting plane. The spacing between the cutting plane and the plate does not exceed 2 mm.

The plate preferably consists of a transparent material, for example PMMA, for good visibility of the section production and evaluation of the removed sections.

In a cutting stroke, the specimen moves with the specimen holder relative to the knife edge and the knife holder. The free spaces and distances between the plate and the specimen moving relative to it are to be set so that a finger joint cannot get between the moving parts.

In most cases, a gap between the knife edge and the plate is unavoidable, so as to ensure the free space required for a successful section production and section removal. However, the width of this gap is not more than 2.5 mm. Since the section sliced from the specimen generally has a thickness on the order of microns, a gap width as well as a spacing between the cutting plane and the plate which are both on the order of millimeters provide adequate protection to the operator while safely avoiding contact between the sections and the plate during the cutting process.

In an advantageous embodiment example of the invention, the plate is arranged pivotably or displaceably on the base member of the knife holder. It is thereby ensured that the blade guard can be brought out of its functional position into a position in which the free access to the specimen is ensured which is necessary for adjustment operations on the specimen. In order to also ensure finger protection in this position, a conventional finger guard is also provided, which can be removed from the cutting edge during the cutting operation.

In a further advantageous embodiment example of the invention, the pivoting or displacement mechanism for the plate is coupled to a switch or micro switch. This switch can, in turn, be coupled electrically to a brake or arresting device for the knife slide or the specimen slide of the microtome, such movement of the knife slide or of the specimen slide is prevented when the plate is pivoted or displaced out its functional position covering the cutting edge of the knife. An unintentional operation of the knife slide during adjustment operations on the microtome is thereby avoided.

The coupling of a switch, which is coupled to a pivotable or displaceable blade guard, to a brake or a motorized cutting drive is also useful with blade guard devices constituted in another manner, and represents a separate invention.

In microtomes which in any case already have a motorized cutting drive, the switch can be arranged in the circuit of the motor for the cutting drive. The load circuit of the drive motor is connected such that an operation of the drive motor is only possible when the plate is located in the functional position covering the knife edge of the knife. It is thereby ensured that an erroneous operation of the operating element such as a foot switch, for example, for the motor drive does not lead to an unintentional switching-on of the cutting drive and thereby bring about the danger of an accident. Possible defects of the operating elements or electrical or electronic components can likewise lead to a comparable danger of an accident, since in the case of corresponding faults the cutting drive can switch on in an uncontrolled manner. Interference influences from the exterior can produce a similar effect. The risks brought about by such faults and interference can thus be markedly reduced by the knife holder according to the invention.

Details of the inventions are explained in greater detail with reference to the embodiment examples shown in the figures.

BRIEF DESCRIPTION OF THE DRAWING

FIGS. 3a and 3b show schematic sketches of a knife holder according to the invention with pivotable (FIG. 3a) or displaceable (FIG. 3b) blade guard;

FIG. 7b shows a section view of the disk microtome of FIG. 7a.

DESCRIPTION OF THE PREFERRED EMBODIMENT

Figure 1:
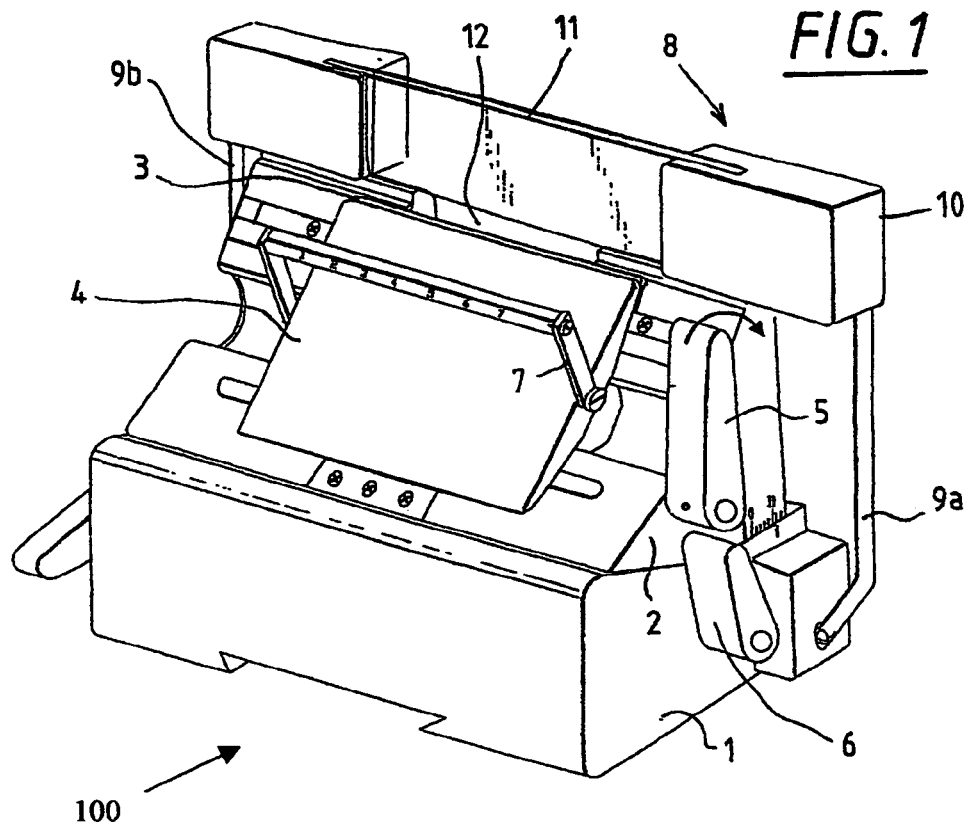
FIG. 1 shows a perspective view of a knife holder according to the invention.

The knife holder seen in FIG. 1 has an essentially conventional construction with, removably mounted on a microtome base, a base member (1) on which a receiving member (2) for the cutting knife (3) is received, rotatable around the cutting edge of the cutting knife (3) for free angle setting. The free angle set at any given time is fixedly set by means of a clamping mechanism (not shown here) which can be operated by means of a lever (6). To fixedly clamp the knife (3), a clamping plate (4) is provided, with which the knife (3) is firmly clamped, in a known manner, between the receiving member (2) and the clamping plate (4) by means of a further clamping mechanism operable by means of a lever (5). The base member (2) has, on the side toward the specimen and in the middle region, a recess in which the specimen to be sectioned can come into contact with the cutting edge of the knife (3) and the specimen can be guided over the knife (3) for section removal. The knife is usually freely accessible precisely in the region of this recess of the receiving member (2), so that a cutting injury can very easily happen to the operator. In order to reduce the risk of such cutting injuries, a pivotable yoke (7) is arranged on the clamping plate (4) and can be pivoted, in the case of mounting and adjusting operations on the microtome or on the specimen, so that the yoke covers the cutting edge of the knife (3). After the conclusion of the adjustment operations and before entering into section removal, this guard yoke (7) must however be pivoted back again into a position in which the knife (3) is accessible to the specimen, since section removal could otherwise not take place.

A described above, the knife holder in FIG. 1 corresponds to a conventional knife holder. According to the present invention, a further blade guard is provided on the base member (1) of the knife holder. The blade guard (8) consists of two arms (91, 9b) which are pivotably arranged at the end sides of the base member (1) and which respectively have a holding jaw (10), with a plate (11) of transparent material connecting the holding jaws (10). The plate (11) preferably consists of PMMA. The plate (11) together which the two holding jaws (10) extends over the whole length of the knife holder, in the direction of the cutting edge of the knife to be received.

Figure 2:
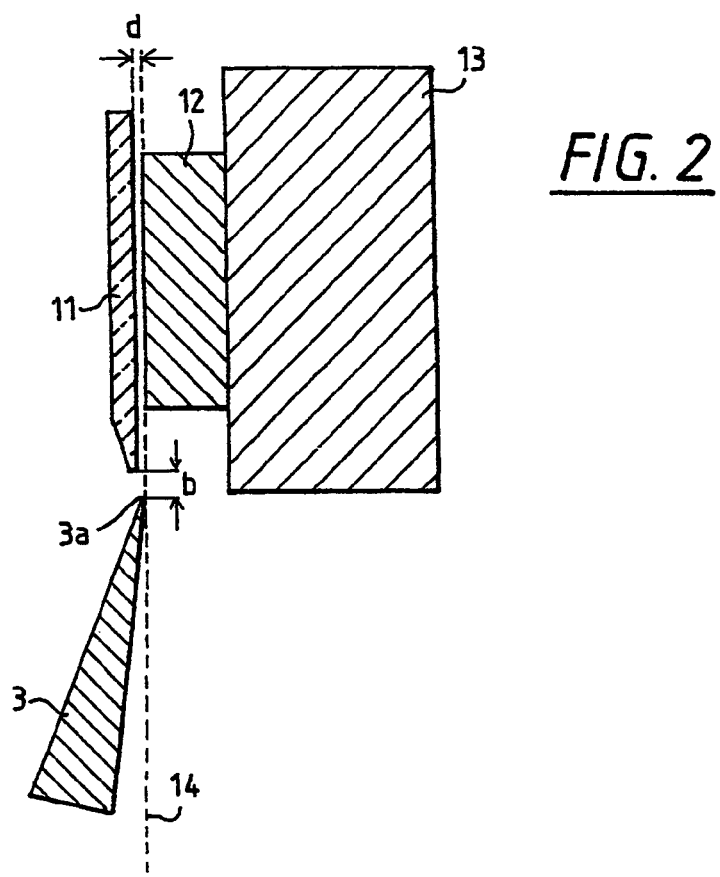
FIG. 2 shows a simplified sectional view through the knife holder in FIG. 1.

As can be gathered from a view with FIG. 2, the plate (11) is arranged, parallel to the cutting plane (14), on the side of the knife carrier remote from the specimen holder (13) and the specimen (12) received on it, and at the same time, is arranged spaced apart from the knife holder on the side of the cutting edge (3a) of the knife. The plate (11) thus faces the cutting edge of the knife. It is ensured by this arrangement of the plate (11) that section removal can take place even with the plate (11) situated in its operating position in which the plate prevents an unintentional gripping of the knife edge (3a). For this purpose, the plate (11) is spaced apart from the cutting plane (14) by a gap (d). In the cutting direction, a small gap (b) is provided between the cutting edge (3a) of the knife and the edge of the plate (11) toward the knife, with a maximum width chosen such that the joint of a person's finger cannot come into contact with the cutting edge (3a) of the knife. The width of the gap (b) is at most 2.5 mm. This gap width is at the same time sufficient for the section taken from the specimen (12) to be able to slide through this gap between the plate (11) and the back face of the knife (3) and to remain lying on the freely accessible back face of the knife (3).

In the embodiment example according to FIG. 1, the plate (11), and thus the whole blade guard, can be pivoted, by pivoting around the pivot axis of the arms (9a, 9b), out of its functional position into an adjustment position in which the specimen is freely accessible for adjustment operations. This pivotability of the plate (11) is shown schematically in FIG. 3a, the plate (11) in the adjustment position being denoted by (11').

In the embodiment example indicated schematically in FIG. 3b, the plate (11) can be moved by linear displacement from its functional position into an adjustment position (11"), in which a free access to the specimen (12) is ensured.

Figure 4:
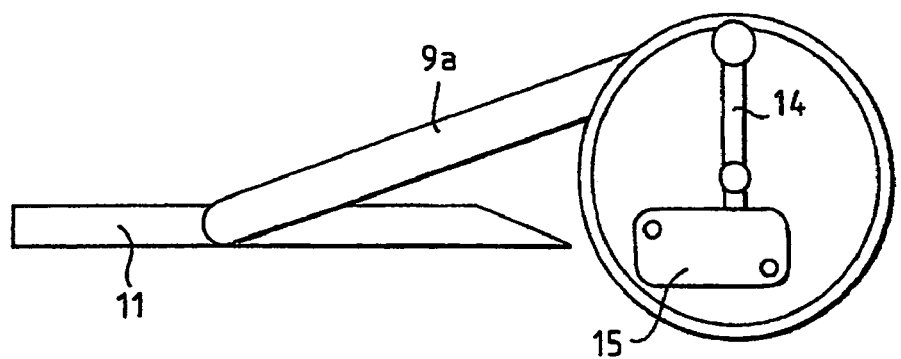
FIG. 4 shows a section through the mounting of a pivoting mechanism for the blade guard according to the invention.

A section through the pivot mounting of the arm (9a) is shown in FIG. 4. The pivoting movement of the arm (9a) is connected to a switch, preferably a micro switch (15), by means of an actuating arm (14). In this embodiment, the micro switch (15) is a normally open contact, that is, the switch (15) is only closed when the arm (9a) is situated in the pivoting position defined by the functional position of the plate (11).

Figure 5:
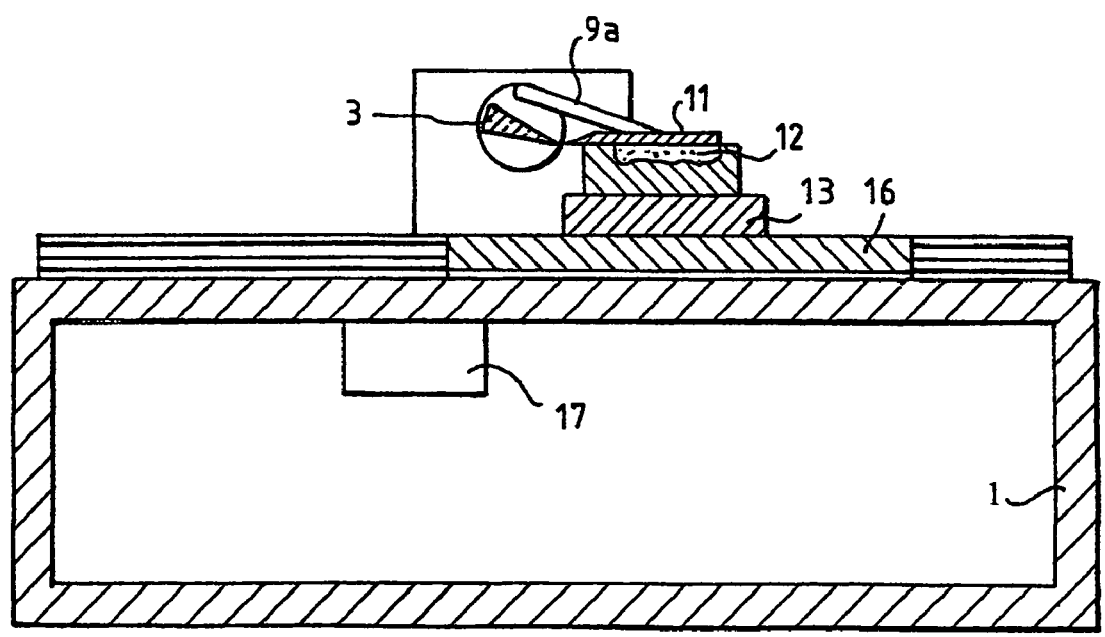
FIG. 5 shows a section through a traversing microtome with a knife holder according to the invention.

In the traversing microtome shown in FIG. 5, the specimen holder (13) with the specimen (12) received on it is horizontally, linearly displaceable on a slide (16) relative to the knife holder with the knife (3) received on it. An electromagnetically actuatable brake device (17) is arranged in the microtome base member (1) and can arrest the slide (16) in its position at any given time. This brake (17) is electrically connected to the switch (15) in the pivot joint of the plate (11) of the knife holder such that the brake (17) only releases the slide (16) when the plate (11) is pivoted into its functional position in which it covers the cutting edge of the knife (3). In all other cases, a movement of the slide (16) is locked by the brake (17), so that an unintentional displacement of the slide during adjustment operations on the specimen (12) or on the knife (3) is prevented.

Figure 6A:
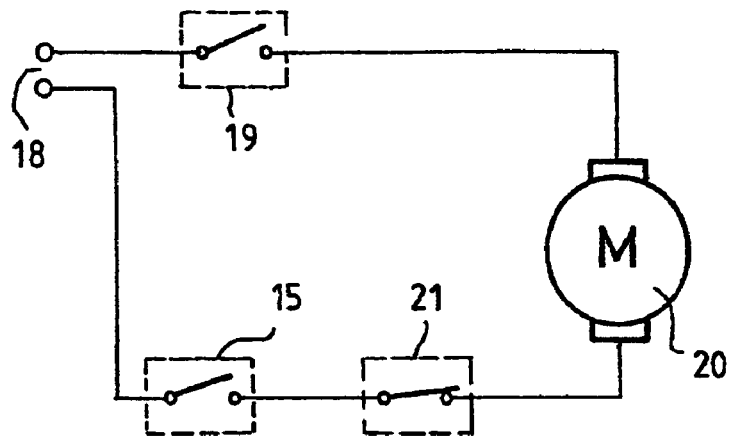
FIGS. 6a-6c show circuits relating to the inclusion of the switch coupled to the pivoting mechanism in the circuit of an arresting device for the microtome slide or the circuit of a motor drive for the microtome slide.
Figure 6B:
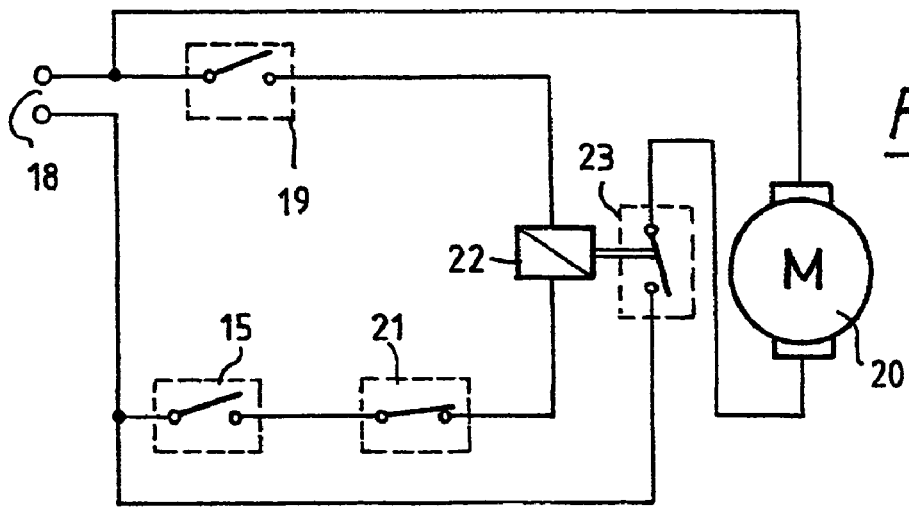
Figure 6C:
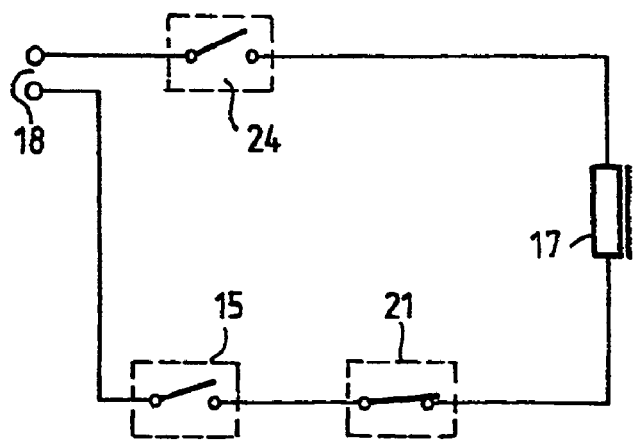

The circuit, not sown in FIG. 5, by means of which the switch (15) on the knife holder is connected to the brake (17) is shown in FIG. 6c. Towards this end, the switch (15) is connected in the circuit of a current source (18), in series with the electromagnet (17) which opens the mechanical drive brake. Furthermore, a further switch (24) on the control panel of the microtome, and an emergency stop switch (21), which is embodied as a normally closed contact, are provided in series with the electromagnet (17) which opens the drive brake. Opening one of the switches (15, 21, 24) effects an immediate arrest of the slide (16). The serial connection with the further switches (21, 24) also enables the arrest of the slide (16) to be effected in the cases in which the blade guard is in its functional position.

The circuit for the motor current of a motorized cutting drive is shown in FIG. 6a. In this circuit also, the switch (15) in the pivot joint of the blade guard is arranged in series in the supply circuit of the motor (20). A switch (19), preferably normally open, for switching the drive motor on, and furthermore an emergency stop switch (21), can be provided here in series in the circuit.

In the embodiment example according to FIG. 6b, the switch (15), together with the start switch (19) on the control panel of the microtome and the emergency stop switch (21), is in the coil circuit of a relay (22). The drive motor for the disk drive (20) is in the load circuit of the relay (22, 23).

Combinations are of course also possible of the embodiment according to FIG. 6c with one according to FIG. 6a or 6b, in that the switch (15) is connected both in the supply circuit of a motor for the disk drive and also in the circuit for an additional brake of the specimen slide or knife slide, so that on opening the switch (15), as well as the drive motor being switched off, and in the additional the slide is also arrested in its present position.

A substantial protective effect results from the inclusion of the switch (15) in the circuit of a brake and/or a motorized cutting drive, since a motor-driven movement of the cutting drive and a danger connected with this is only possible when the blade guard is located on its functional position. In this functional position, however, cutting injuries are precluded, since the cutting edge of the knife is not at all accessible to the operator. The risk of cutting injuries on the microtome knife is thereby considerably reduced.

Figure 7A:
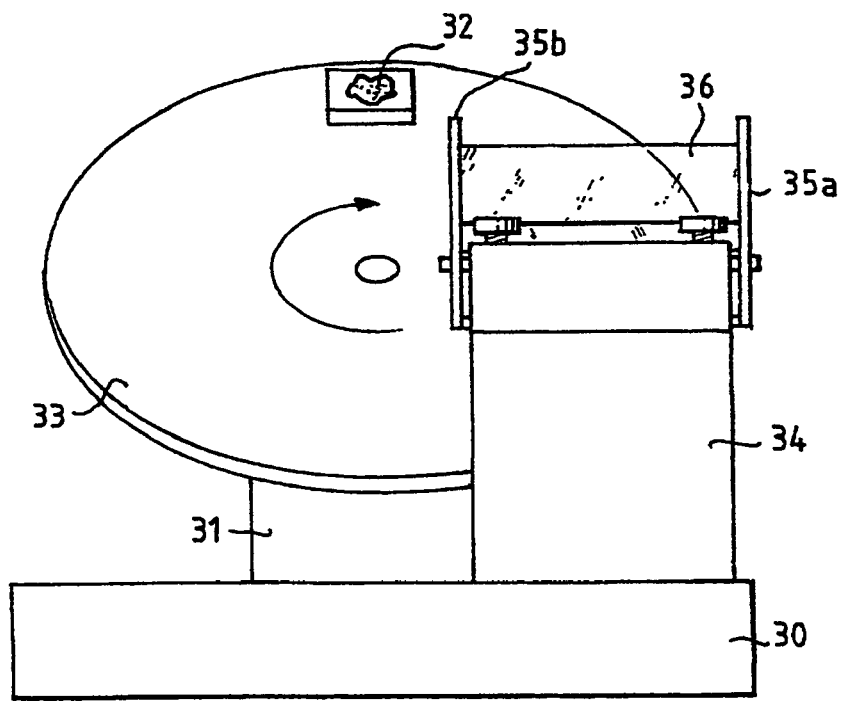
FIG. 7a shows a perspective view of a disk microtome with a knife holder according to the invention.
Figure 7B:
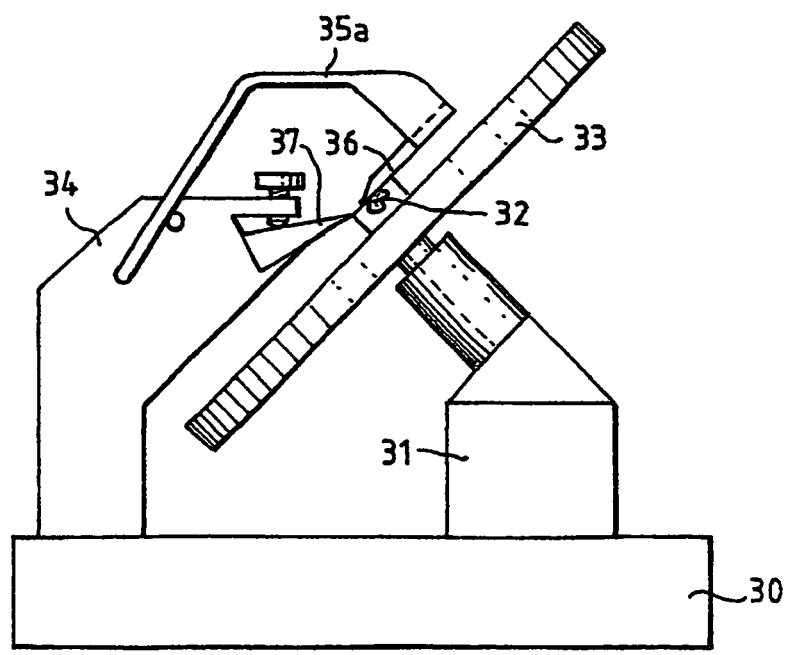

In the embodiment example in FIG. 7, the knife holder according to the invention is shown in connection with a disk microtome. This disk microtome consists of a base plate (30) on which a circular disk (33) for receiving the specimen (32) is arranged by means of a column (31). The disk (33) can be rotated by a motor drive, not shown here. Furthermore, the base portion of the knife holder (34) with the knife (37) received in it, is arranged on the base plate (30). The previously described blade guard with the arms (35a, 35b) and the plate (36) connecting the arms is pivotably arranged on the base portion of the knife holder (34). Cutting injuries on the knife are largely excluded by the knife holder according to the invention in such a disk microtome. The coupling of the switch connected to the pivoting mechanism of the guard device with the drive motor for the disk (33) only permits rotation of the disk (33) when the plate (36) is situated in its functional position, covering the knife (37).

The invention claimed is:

1. A microtome for use by an operator to slice-off a thin section from a specimen, the thin section having a substantially uniform thickness on the order of microns, the microtome comprising:

a support base;

a knife cooperating with said support base, said knife having a cutting edge defining a cutting plane, said knife also having a back surface facing in an upward direction away from said cutting plane at a first side of said cutting plane;

a specimen holder on which the specimen is mounted, said specimen holder disposed at a second side of said cutting plane opposite to said first side of said cutting plane;

means, mounted to said support base, for moving said specimen holder parallel to said cutting plane and towards said cutting edge to slice-off the section from the specimen; and a guard plate disposed above said knife edge at said first side of said cutting plane, said guard plate cooperating with said support base and having a front face disposed parallel to and at a separation of not more than 2 mm from said cutting plane during slicing of the specimen, said guard plate having a front edge spaced apart from and extending substantially parallel to said cutting edge, wherein said guard plate, said knife, said support base, and said specimen holder are disposed, structured and dimensioned such that the thin section comes to rest on said back surface of said knife where it is freely accessible for removal by the operator, wherein said guard plate prevents a finger of the operator from coming into contact with said knife edge during slicing of the thin section and during removal of the thin section while avoiding any contact between said plate and the specimen and between said plate and the thin section wherein said plate is moveable from a first position where the plate extends parallel to said cutting plane and is positioned in front of the cutting edge of said knife, and a second position where said plate is moved away from said knife, a switch for sensing when the plate is in the first position and permitting the moving of the specimen holder only when the plate is in the first position.

2. The microtome of claim 1, wherein said plate comprises a transparent material.

3. The microtome of claim 1, wherein said plate can be pivoted away from said cutting plane to said second position to permit operator access to said knife.

4. The microtome of claim 1, wherein said plate can be displaced substantially parallel to said cutting plane to said second position to permit operator access to said knife.

* * * * *